(12) United States Patent
Nauber et al.

(10) Patent No.: US 8,414,751 B2
(45) Date of Patent: Apr. 9, 2013

(54) GAS SENSOR WITH TEST GAS GENERATOR

(75) Inventors: Andreas Nauber, Stockelsdorf (DE); Michael Sick, Timmendorfer Strand (DE); Julia Danckert, Mölln (DE); Peter Tschuncky, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 98 days.

(21) Appl. No.: 12/888,598

(22) Filed: Sep. 23, 2010

(65) Prior Publication Data

US 2011/0108418 A1    May 12, 2011

(30) Foreign Application Priority Data

Nov. 12, 2009  (DE) .......... 10 2009 052 957

(51) Int. Cl.
*G01N 27/413* (2006.01)
(52) U.S. Cl. ......... 204/416; 204/415; 204/431; 204/432
(58) Field of Classification Search .......... 204/400–402, 204/406–420, 430–435
See application file for complete search history.

(56) References Cited

U.S. PATENT DOCUMENTS

| | | | |
|---|---|---|---|
| 3,775,279 A * | 11/1973 | Boley ............... | 204/242 |
| 4,151,739 A | 5/1979 | Breuer et al. | |
| 4,742,708 A | 5/1988 | Porter | |
| 5,667,558 A | 9/1997 | Bryan et al. | |
| 5,668,302 A * | 9/1997 | Finbow et al. ......... | 73/23.2 |
| 6,635,160 B1 | 10/2003 | Dodgson | |
| 2006/0266098 A1 * | 11/2006 | Eickhoff et al. ...... | 73/1.06 |
| 2006/0283707 A1 | 12/2006 | Kuhn | |
| 2008/0277290 A1 * | 11/2008 | Jones ................. | 205/775 |
| 2008/0282765 A1 | 11/2008 | Bonne et al. | |

FOREIGN PATENT DOCUMENTS

| | | |
|---|---|---|
| DE | 102005028246 A1 | 12/2006 |
| EP | 0 744 620 A1 | 11/1996 |
| EP | 1031031 A1 | 8/2000 |
| GB | 2 254 696 | 10/1992 |
| GB | 2356708 A | 5/2001 |
| WO | WO 9924826 A1 | 5/1999 |

* cited by examiner

*Primary Examiner* — Keith Hendricks
*Assistant Examiner* — Bach Dinh
(74) *Attorney, Agent, or Firm* — McGlew and Tuttle, P.C.

(57) ABSTRACT

A gas sensor (100) in a sensor housing (1) has a gas-permeable membrane (7) for the inlet of a gas sample to be analyzed to a measuring electrode (6). The gas sensor (100) is provided with a test gas generator (18), which has a generator housing (8). The generator housing (8) is fastened in the area of the gas-permeable membrane (7) and has a central gas outlet opening (21) for the gas sample to pass into the sensor and has outlet openings (19) directed towards the gas-permeable membrane (7) for the test gas.

20 Claims, 3 Drawing Sheets ized by the requirements imposed on the desired precision of the gas sensor. National specifications require checking of gas sensors at regular intervals.

GAS SENSOR WITH TEST GAS GENERATOR

CROSS REFERENCE TO RELATED APPLICATIONS

This application claims the benefit of priority under 35 U.S.C. §119 of German Patent Application DE 10 2009 052 957.8 filed Nov. 12, 2009, the entire contents of which are incorporated herein by reference.

FIELD OF THE INVENTION

The present invention pertains to a gas sensor with a test gas generator.

BACKGROUND OF THE INVENTION

Gas warning devices with a gas sensor must be subjected to function tests at regular intervals. For example, failure of a gas sensor may occur due to blockage of the gas inlet or inactivation of the sensor element. Proper function of a gas sensor is best tested by admitting a target gas, while the entire functional chain from the gas feed to the signal generation is tested.

Commercially available gas sensors have a sensitivity drift with respect to the gas component to be detected. This characteristic of gas sensors cannot be described or predicted by mathematical formulas. It is therefore necessary to calibrate gas sensors within certain time intervals with a target gas of a known concentration. The duration of the interval between calibrations is determined by the requirements imposed on the desired precision of the gas sensor. National specifications require checking of gas sensors at regular intervals.

The effort needed for carrying out a function test and calibration operations is great. For example, testing means, e.g., in the form of pressurized gas containers, preferably containing the target gases, must be kept ready, transported to the gas sensor within the preset duration of use of the gas mixture and finally introduced there into the gas inlet of the gas sensor to be tested through suitable devices, e.g., pumps, valves, calibration adapters and/or flow controllers. To guarantee short test times and sufficient test gas concentrations, dead space volumes and undefined arriving flow conditions must be avoided.

To circumvent these drawbacks, it was already proposed in GB 22 54 696 A1 to accommodate a gas generator together with a gas sensor in a common housing. The common housing is defined here against the gas to be measured by a gas-permeable membrane. Even though the occasional activation of the gas generator makes it possible to test the sensor function with a synthetic gas, the dead space volumes present in the arrangement do compromise the function test. Furthermore, this testing method does not provide any information on the state of the outer, gas-permeable membrane. The path of the gas to the detector electrode thus remains untested.

Test gas is sent through a membrane, which is also connected to the gas generator and the gas sensor, in the gas sensor corresponding to EP 0 744 620 B1. The state of the outer membrane granting access of the gas to the detector electrode can be inferred with difficulty only in this case as well.

In the measuring device corresponding to U.S. Pat. No. 6,635,160 B1, the test gas is injected into a test gas chamber in the interior of the sensor housing, which chamber is arranged downstream of the outer gas inlet. However, the gas inlet from the outside to this chamber and hence also to the detector electrode of the sensor remain untested here as well.

A diagnostic method for gas sensors, in which test gas is pressed through an aperture to a sensor, delivered by adding a propellant or moved to the sensor by thermal expansion, is described in U.S. Pat. No. 4,151,739.

All these embodiments share the drawback that the entire path of the gas sample to the detector electrode is ultimately not tested or means must be provided by mechanically complicated constructions for delivering the test gas to the sensor.

SUMMARY OF THE INVENTION

The basic object of the present invention is to provide an improved function test for a gas sensor.

According to the invention, a device is provided with a gas sensor in a sensor housing, which housing has a gas-permeable membrane for the gas sample to be analyzed and a measuring electrode. The device is also provided with a test gas generator, which has a generator housing, which is fastened in the area of the gas-permeable membrane, has a gas inlet opening for the gas sample and has outlet openings directed towards the gas-permeable membrane for test gas.

The gas sensor may be an electrochemical gas sensor with a reference electrode in an electrolyte in the sensor housing in addition to the measuring electrode. The test gas generator may be an electrochemical gas generator.

The outlet openings of the generator housing may be closed with a gas-permeable ring membrane.

Provisions are made according to the present invention for arranging a test gas generator upstream of the gas-permeable membrane of the gas sensor. The test gas produced by the test gas generator reaches the measuring electrode of the gas sensor from outlet openings of the generator housing via the gas-permeable membrane of the gas sensor. To minimize dead space volumes, the outlet openings of the generator housing and the gas-permeable membrane of the gas sensor are arranged directly opposite each other. The advantage of this arrangement is that the test result is affected by external effects, especially by wind, only slightly. Typical sensor parameters, e.g., response time, sensitivity or drift, are affected only negligibly at best. The generator housing is designed such that there is a gas inlet opening for the measured gas to be analyzed preferably in the middle of the test gas generator. Both the measured gas and the test gas produced by the gas generator reach the measuring electrode via the gas-permeable membrane of the gas sensor.

Thus, the same gas path that is also used by the measured gas is tested with the test gas. The analysis of the sensor signal is interrupted for the short test times of a few seconds only, during which the test gas is electrochemically generated. The generator housing has a curved shape, which is closed in itself. Thus, it may be ring-shaped, oval, elliptical, rectangular or square in such a way that a gas inlet opening for the measured gas to be analyzed is present preferably in the middle of the housing. The shape of the generator housing is not limited to said variants, but other housing shapes, with which a gas inlet opening for the measured gas to be analyzed can be embodied, are conceivable as well.

The generator housing advantageously contains as the test gas source a pellet consisting of silver sulfide with a platinum mesh connected as a cathode and a platinum electrode as an anode for the electrochemical generator of hydrogen sulfide ($H_2S$). $H_2S$ is generated by applying a voltage between the anode and the cathode.

The axial distance between the outlet openings of the test gas generator and the gas-permeable membrane is advantageously in a range of 10 μm to 10 mm. This means that the test gas generator directly admits gas to the gas-permeable membrane of the electrochemical gas sensor.

An actuating unit with a corresponding electronic system is preferably present for the electrodes of the electrochemical gas sensor and the electrodes of the test gas generator.

The gas inlet opening at the test gas generator, which opening is arranged upstream of the gas-permeable membrane of the gas sensor, is preferably provided with a dust filter in order to prevent the gas-permeable membrane from becoming contaminated.

The sensor housing is preferably designed as a mount for receiving the test gas generator in the area of the gas-permeable membrane. The dust filter is located at the free end of the mount, so that the measured gas can only reach the gas-permeable membrane of the gas sensor via the dust filter.

When test gas is being generated with the test gas generator during the test time, this gas diffuses both to the measuring electrode of the gas sensor and, via the dust filter, into the environment. The part of the test gas diffusing into the environment is not therefore available for the measurement electrode for signal generation. An increased measured signal is obtained at the gas sensor in case of a contaminated dust filter, from which information can be obtained concerning the gas permeability of the dust filter.

An exemplary embodiment is shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
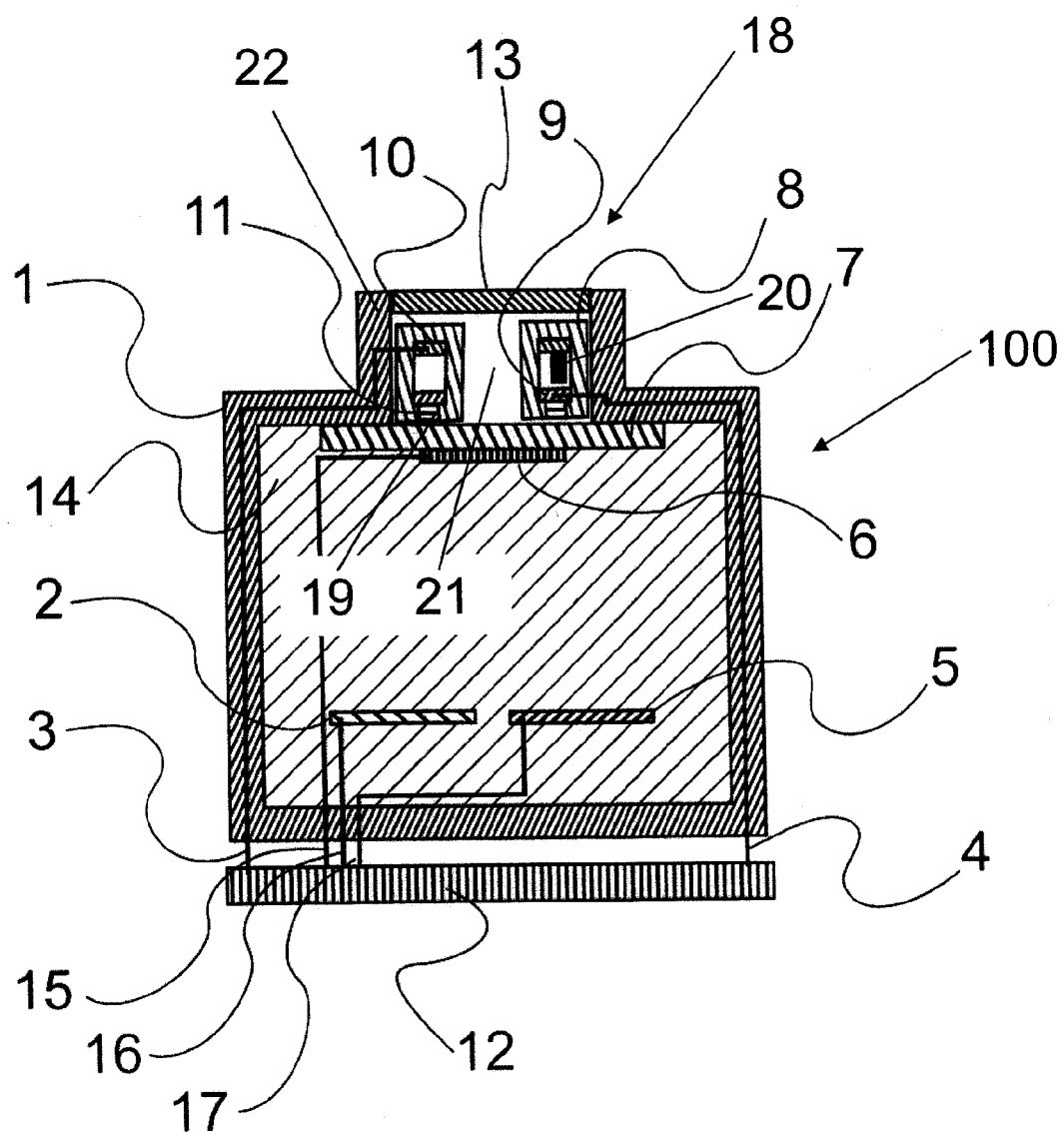
FIG. 1 is a longitudinal sectional view of an electrochemical gas sensor with a test gas generator according to the invention.

Referring to the drawings in particular, FIG. 1 schematically shows an electrochemical gas sensor 100 for detecting hydrogen sulfide with a test gas generator 18 for hydrogen sulfide. The gas sensor 100 comprises a sensor housing 1, into which two, but preferably three precious metal electrodes 2, 5, 6 in the form of a measuring electrode 6, an auxiliary electrode 2 and a reference electrode 5, an electrolyte 14 and corresponding contact wires 15, 16, 17, preferably platinum wire, for the electrodes 2, 5, 6 are inserted (contact wire 15 leading from measuring electrode 6 to actuating electronic unit 12, contact wire 16 leading from auxiliary electrode 2 to actuating electronic unit 12 and contact wire 17 leading from reference electrode 5 to actuating electronic unit 12). The sensor housing 1 is closed on the front side by a gas-permeable membrane 7, which is not permeable for the electrolyte 4, preferably a membrane consisting of a fluorinated, porous polymer, which limits the interior space of the sensor from the surrounding atmosphere. The measuring electrode 6 is located in the interior space of the sensor directly behind said gas-permeable membrane 7. The electrodes 2, 5, 6 are connected to an actuating electronic unit 12 to analyze the signal of the measuring electrode 6.

Furthermore, at least two electric contact wires 3, 4 for the test gas generator 18, which are used to connect the actuating electronic unit 12 to a cathode 9 and to an anode 10 of the test gas generator 18, are led through in the sensor housing 1. The test gas generator 18 comprises a radially symmetrical, ring-shaped generator housing 8, with outlet openings 19, which are closed by a gas-permeable ring membrane 11. A pellet 20 consisting of silver sulfide and sulfur at a weight ratio of 1:1 is connected to a platinum mesh connected as a cathode 9 and is reacted electrochemically. An electrode consisting of platinum is used as an anode 10. Cathode 9 and anode 10 are connected to the actuating electronic unit 12 by means of the contact wires 3, 4 and are in connection with a power source, not shown more specifically. Electrolysis of the pellet 20 is carried out in sulfuric acid as an electrolyte by means of the power source and metallic silver is formed besides free sulfide ions. The addition of elemental sulfur makes it possible for the silver to be immediately reacted again into sulfide and to become again involved in the reaction. The reactions taking place are:

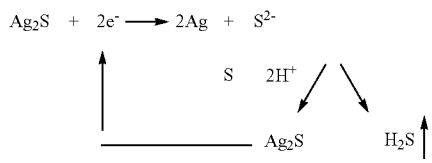

The $H_2S$ formed at cathode 9 leaves the generator housing 8 of the test gas generator 18 through the gas-permeable ring membrane 11. The outlet openings 19 of the test gas generator 18 face the gas-permeable membrane 7 of gas sensor 100, as a result of which interferences due to, e.g., the effect of wind or rain can be minimized. The on time (=electrolysis time) of the test gas generator 18 determines the absolute quantity of test gas formed and hence also the $H_2S$ concentration present at the gas sensor 100.

A centrally located gas inlet opening 21 of the test gas generator 18 is protected by a dust filter 13, preferably one made of porous polytetrafluroethylene (PTFE-TEFLON®) or polyethylene. The sensor housing 1 is designed in the area of the gas-permeable membrane 7 as a mount 22, which is used to receive the test gas generator 18. The top side of mount 22 is closed with the dust filter 13. The measured gas reaches the gas-permeable membrane 7 of gas sensor 100 via the dust filter 13 and the gas outlet opening 21.

Figure 2:
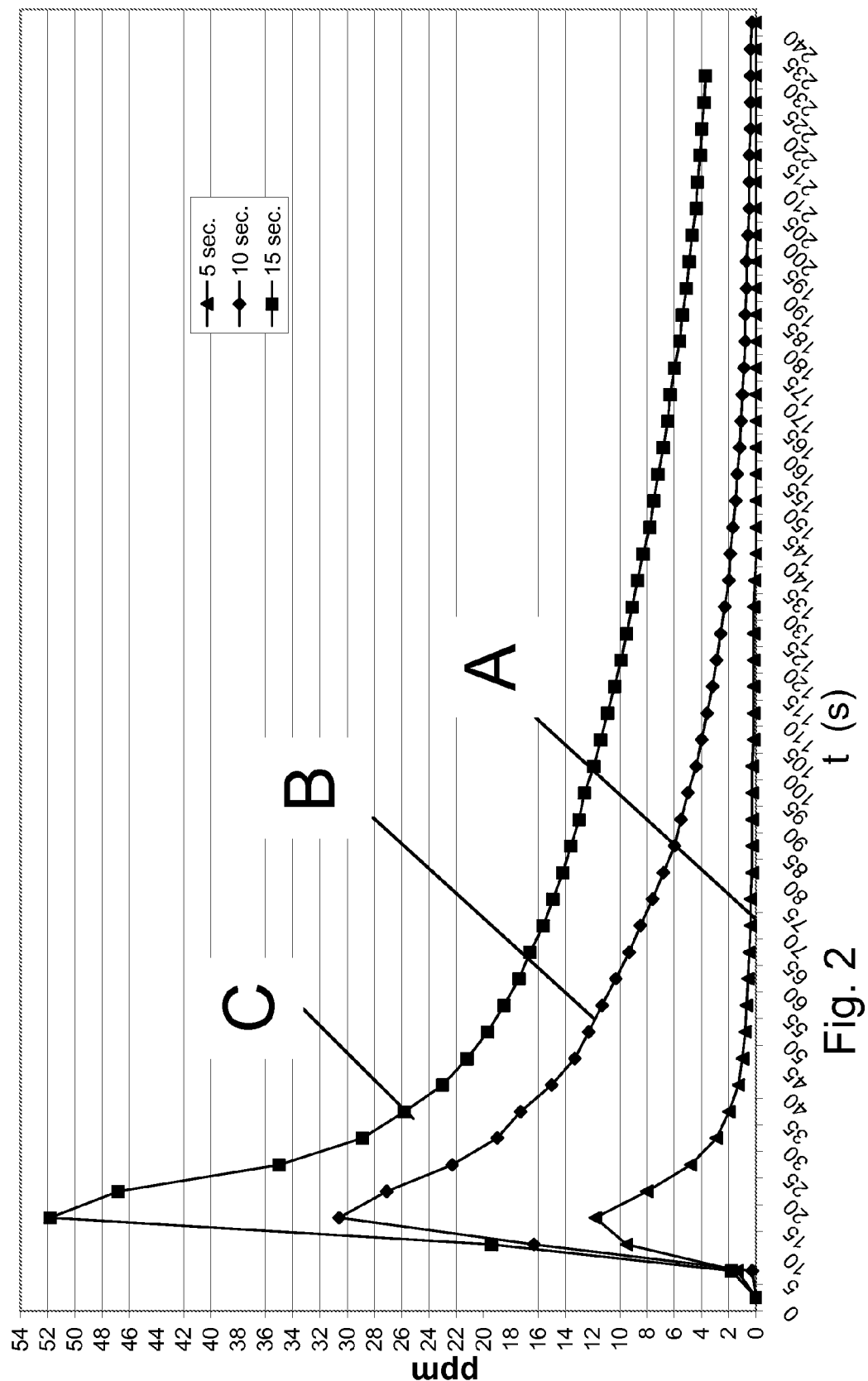
FIG. 2 is a view showing a signal pattern of the gas sensor for different activation times of the test gas generator.

FIG. 2 shows as an example the time curve of the sensor current as a function of the duration of activation of the test gas generator 18. The time in seconds is plotted on the abscissa and the concentration indication of the gas sensor 100 in parts per million (ppm) is plotted on the ordinate. The lower curve A indicates an activation time of 5 sec, the middle curve B an activation time of 10 sec and the top curve C an activation time of 15 sec.

A very short test time of less than 60 sec can be obtained due to the minimized dead space volumes of the arrangement. Furthermore, monitoring concerning the target gas at a high concentration can also be guaranteed during the test due to the suitable generation of a test gas of a low concentration.

Figure 3:
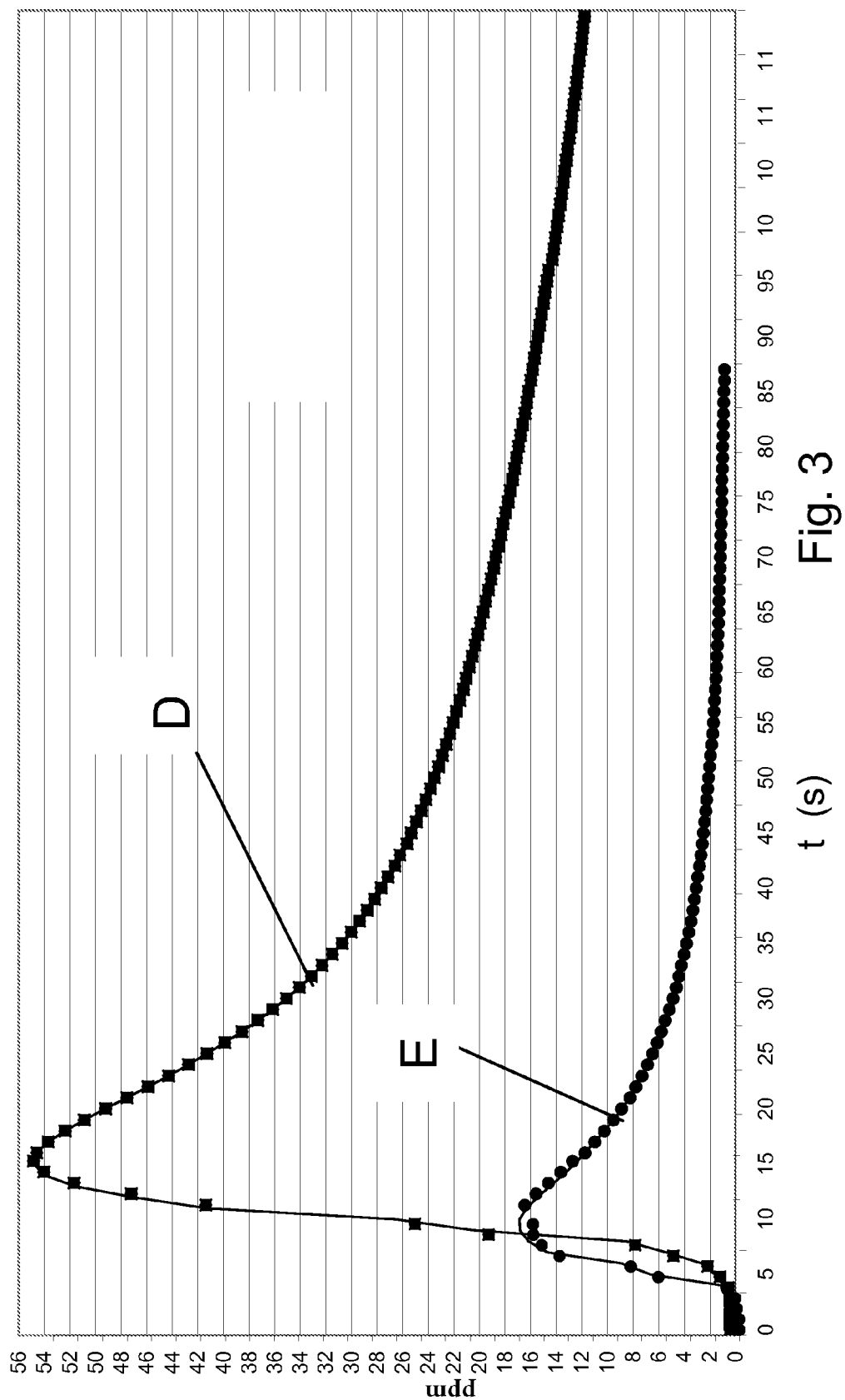
FIG. 3 is a view showing the signal pattern corresponding to FIG. 2 with dust filters loaded to different extents.

Another advantage of the arrangement is the simple detection of a contaminated dust filter 13. The test gas generated diffuses both to the measuring electrode 6 and, via the dust filter 13, into the environment in front of the gas sensor 100. This component is not available for the measuring electrode 6. FIG. 3 shows the measured signal for a filter 13 loaded with dust, curve D, and for a non-contaminated dust filter 13, curve E for comparison. If the dust filter 13 is contaminated, diffusion into the environment is prevented from occurring. This portion can now likewise be reacted by the measuring electrode 6. The signal corresponding to curve D is therefore increased compared to the normal state, curve E.

The contaminated dust filter 13 leads, furthermore, to a delayed decay characteristic after the end of the test gas generation, because the gas exchange with the environment is hindered. This characteristic can be unambiguously determined by a corresponding analysis.

While specific embodiments of the invention have been described in detail to illustrate the application of the principles of the invention, it will be understood that the invention may be embodied otherwise without departing from such principles.

Appendix

| LIST OF REFERENCE NUMBERS | |
|---|---|
| 1 | Sensor housing |
| 2 | Auxiliary electrode |
| 3, 4 | Contact wire |
| 5 | Reference electrode |
| 6 | Measuring electrode |
| 7 | Gas-permeable membrane |
| 8 | Generator housing |
| 9 | Cathode |
| 10 | Anode |
| 11 | Gas-permeable ring membrane |
| 12 | Actuating electronic unit |
| 13 | Dust filter |
| 14 | Electrolyte |
| 15, 16, 17 | Contact wire |
| 18 | Test gas generator |
| 19 | Outlet opening |
| 20 | Pellet |
| 21 | Gas inlet opening |
| 22 | Mount |
| 100 | Gas sensor |

What is claimed is:

1. A device comprising:
A gas sensor with a sensor housing, a gas-permeable membrane for allowing a gas sample to be analyzed to enter the sensor housing and a measuring electrode in said sensor housing; and
A test gas generator with a generator housing fastened to the sensor housing in an area of the gas-permeable membrane, the generator housing having a gas inlet opening for the gas sample, a central gas through passage extending from the inlet opening to the gas permemeable membrane and gas outlet openings directed towards the gas-permeable membrane for test gas, said gas outlet openings and said gas-permeable membrane being disposed directly opposite one another, said generator housing having a self-enclosed shape with said gas inlet opening in a middle region of said generator housing, said test gas generator surrounding said central gas through passage.

2. A device in accordance with claim 1, wherein the gas sensor is an electrochemical gas sensor and has electrolyte in said sensor housing and a reference electrode in said electrolyte, said measuring electrode being in contact with said electrolyte and said gas-permeable membrane, said measuring electrode having a first region located opposite said gas inlet opening, said gas outlet openings overlapping a second region of said measuring electrode, said first region of said measuring electrode being adjacent to said second region of said measuring electrode.

3. A device in accordance with claim 1, wherein said outlet openings of said generator housing are closed with a gas-permeable ring membrane.

4. A device in accordance with claim 1, wherein said test gas generator is an electrochemical gas generator.

5. A device in accordance with claim 1, wherein said generator housing has a pellet consisting essentially of silver sulfide between an anode and a cathode as a test gas source for the electrochemical generation of $H_2S$.

6. A device in accordance with claim 5, further comprising an actuating electronic unit wherein:
said test gas generator is an electrochemical gas generator with electrodes; and
said actuating electronic unit is provided for the electrodes of the electrochemical gas sensor and the electrode of the test gas generator.

7. A device in accordance with claim 1, wherein an axial distance between said outlet openings of said test gas generator and said gas-permeable membrane is in a range from 10μm to 10 mm.

8. A device in accordance with claim 1, further comprising a dust filter provided in or covering the gas inlet opening.

9. A device in accordance with claim 1, wherein the sensor housing comprises a mount for receiving the test gas generator in an area of the gas-permeable membrane.

10. A device comprising:
A gas sensor housing with an interior space and an opening;
A gas-permeable membrane closing the opening of the interior space of the gas sensor and a reference electrode in contact with the electrolyte;
A test gas generator connected to the gas sensor housing adjacent to the gas-permeable membrane, the test gas generator defining a central gas through passage for gas to be analyzed to pass through the central gas through passage and through the gas-permeable membrane into the interior space of the gas sensor housing, the test gas generator comprising a generator housing having a plurality of outlet openings for directing test gas out of the test gas generator and towards the gas-permeable membrane, said central gas through passage being located in a central area of said generator housing, said gas-permeable membrane being adjacent to said plurality of outlet openings, said generator housing comprising a self-enclosed shape, wherein said test gas generator extends around said central gas through passage.

11. A device in accordance with claim 10, wherein said outlet openings of said generator housing are closed with a gas-permeable ring membrane, said measuring electrode engaging at least a portion of one side of said gas-permeable membrane, at least one portion of said measuring electrode being opposite said central gas through passage, said plurality of outlet openings overlapping at least another portion of said measuring electrode, said at least one portion of said measuring electrode being adjacent to said another portion of said measuring electrode.

12. A device in accordance with claim 11, wherein said test gas generator is an electrochemical gas generator with electrodes, said gas-permeable membrane being in contact with said electrolyte.

13. A device in accordance with claim 12, wherein a pellet silver sulfide is disposed in said generator housing between the electrodes in the form of an anode and a cathode, said pellet silver sulfide forming a test gas source for the electrochemical generation of $H_2S$ via said anode and said cathode.

14. A device in accordance with claim 12, further comprising an actuating electronic unit wherein the actuating electronic unit is connected to the measuring electrode unit reference electrode and the electrodes of the test gas generator.

15. A device in accordance with claim 10, wherein a distance between said outlet openings of said test gas generator and said gas-permeable membrane is in a range from 10μm to 10 mm.

16. A device in accordance with claim 10, wherein the sensor housing comprises:
a wall structure defining the interior space of the gas sensor housing and defining the opening with an outer surface surrounding the opening; and
a mount extending from the outer surface and extending about the opening, the mount receiving the test gas generator in an area of the gas-permeable membrane.

17. A device in accordance with claim 16, further comprising a dust filter provided in or covering a mount gas inlet opening of the mount.

18. A device comprising:
a gas sensor housing with a wall structure defining a gas sensor housing interior space and defining an outer surface with an opening;
a mount extending from the outer surface and extending annularly about the opening;
a gas-permeable membrane closing the opening of the gas sensor housing interior space;
electrolyte in the gas sensor housing interior space;
a measuring electrode in contact with the electrolyte in the gas sensor housing interior space and a reference electrode in contact with the electrolyte in the gas sensor housing interior space; and
an annular test gas generator, the mount receiving the test gas generator in an area of the gas-permeable membrane, the test gas generator defining a central gas through passage for gas to be analyzed to pass through the central gas through passage and through the gas-permeable membrane into the gas sensor housing, the test gas generator having a plurality of outlet openings in a ring pattern facing the gas-permeable membrane for directing test gas out of the test gas generator and towards the gas-permeable membrane, said gas-permeable membrane being directly adjacent to said plurality of outlet openings, said test gas generator comprising a generator housing, said central gas through passage being located at a central region of said generator housing, said annular test gas generator extending in a circumferential direction about said central gas through passage, whereby said annular test gas generator surrounds said central gas through passage.

19. A device in accordance with claim 18, wherein:
the outlet openings of the test gas generator are closed with a gas-permeable ring membrane, said measuring electrode being in contact with said gas-permeable membrane, at least a first portion of said measuring electrode being opposite said central gas through passage, one or more of said plurality of outlet openings overlapping at least a second portion of said measuring electrode, said at least said first portion being adjacent to said at least said second portion;
the test gas generator is an electrochemical gas generator with electrodes; and
a distance between said outlet openings of said test gas generator and said gas-permeable membrane is in a range from 10μm to 10 mm.

20. A device in accordance with claim 18, further comprising:
an actuating electronic unit wherein the actuating electronic unit is connected to the measuring electrode and the reference electrode and the electrodes of the test gas generator, at least a portion of said gas sensor housing wall being in contact with said gas-permeable membrane, said gas-permeable membrane being in contact with said electrolyte, said gas-permeable membrane being impermeable to said electrolyte; and
a dust filter provided in or covering a mount gas inlet opening of the mount.

* * * * *